United States Patent
Barreto et al.

(10) Patent No.: US 11,955,206 B2
(45) Date of Patent: Apr. 9, 2024

(54) PERSONALITY GENETICS

(71) Applicant: Pheramor, Inc., Houston, TX (US)

(72) Inventors: Brittany Barreto, Houston, TX (US); Bin Huang, Houston, TX (US)

(73) Assignee: Pheramor, Inc.

(*) Notice: Subject to any disclaimer, the term of this patent is extended or adjusted under 35 U.S.C. 154(b) by 0 days.

(21) Appl. No.: 18/064,028

(22) Filed: Dec. 9, 2022

(65) Prior Publication Data

US 2023/0105314 A1  Apr. 6, 2023

Related U.S. Application Data

(63) Continuation of application No. 16/460,577, filed on Jul. 2, 2019, now Pat. No. 11,551,787.

(51) Int. Cl.
| | | |
|---|---|---|
| *G06F 16/95* | (2019.01) | |
| *G06F 16/9535* | (2019.01) | |
| *G16B 20/00* | (2019.01) | |
| *G16B 20/20* | (2019.01) | |
| *G16B 20/40* | (2019.01) | |
| *G16B 40/00* | (2019.01) | |
| *G16B 50/00* | (2019.01) | |
| *G16H 50/30* | (2018.01) | |

(52) U.S. Cl.
CPC ......... *G16B 40/00* (2019.02); *G06F 16/9535* (2019.01); *G16B 20/00* (2019.02); *G16B 20/20* (2019.02); *G16B 20/40* (2019.02); *G16B 50/00* (2019.02); *G16H 50/30* (2018.01)

(58) Field of Classification Search
CPC ...... G06F 16/9535; G16B 20/20; G16H 50/30
See application file for complete search history.

(56) References Cited

U.S. PATENT DOCUMENTS

| | | | |
|---|---|---|---|
| 2013/0035912 A1* | 2/2013 | Margines | G06N 5/04 703/2 |
| 2014/0081650 A1* | 3/2014 | Sachs | G16H 10/20 705/2 |
| 2014/0359439 A1* | 12/2014 | Lyren | G06F 16/9538 707/706 |
| 2016/0086089 A1* | 3/2016 | Ritchie | G06N 7/00 706/11 |
| 2016/0140240 A1* | 5/2016 | Allen | G06F 16/9535 707/733 |
| 2017/0053082 A1* | 2/2017 | Pereira | G16H 50/50 |
| 2017/0364605 A1* | 12/2017 | Sobel | G16H 10/20 |
| 2018/0181701 A1* | 6/2018 | Niculescu | C12Q 1/6883 |
| 2018/0366142 A1* | 12/2018 | Ashoori | A61B 5/11 |
| 2019/0160251 A1* | 5/2019 | Shanmugam | A61M 21/02 |
| 2019/0266471 A1* | 8/2019 | Rakshit | A61B 5/1116 |
| 2021/0333265 A1* | 10/2021 | Selaru | G01N 33/5091 |

* cited by examiner

*Primary Examiner* — Eliyah S. Harper
(74) *Attorney, Agent, or Firm* — Kearney, McWilliams & Davis, PLLC; William Yarbrough

(57) ABSTRACT

The present invention provides a novel approach to matching personality traits, as determined through observational or self-assessment reporting in combination with specific loci and identifiable variations within an individual's nucleotide sequence in the form of SNPs. The present invention further utilizes an individual's cyber footprint, in combination with SNPs and traditional assessment and self-assessment techniques, to define a testing and reinforcement mechanism for strengthening the interdependence and accuracy of each type of reporting in order to bolster the reliability of each alone and in combination.

19 Claims, No Drawings

PERSONALITY GENETICS

CROSS-REFERENCE TO RELATED APPLICATIONS

U.S. Provisional Patent Application No. 62/693,193 Filed Jul. 2, 2018 U.S. Nonprovisional patent application Ser. No. 16/460,577 Filed Jul. 2, 2019

FEDERALLY SPONSORED RESEARCH AND DEVELOPMENT

Not Applicable

INCORPORATION BY REFERENCE

Not Applicable

SPECIFICATION

Field of the Invention

The present invention relates to contextualized genetics testing and valuation that combines direct observation, self-assessment and identified and identifiable genetically heritable traits in order to more accurately define and describe the components of an individual's personality makeup and to delineate and describe degrees of compatibility between individuals.

Background

Personality, according to the American Psychological Association, refers to individual differences in characteristic patterns of thinking, feeling and behaving. And, as most experts agree, differences in an individual's personalities is a mix of both internal (genetic) forces and external (environmental) forces. Unfortunately, to what degree each force influences an individual is amorphous at best and to date has only been described through ill-defined measurements relying on either (1) direct observation or (2) self-reporting, the primary means almost entirely being the latter in the form of subjective self-assessment.

While self-assessment is an invaluable tool for improvement in one's own life and in terms of evaluating an individual's interpersonal and professional life, self-analyzing, through self-assessment testing, yet contains intrinsic conflicts and biases that are inherently incorporated into such testing's diagnostic model. Individuals may fall prey to any number of conscious and subconscious influencers that conflate the results, underrepresent certain factors within the testing model and bring into question these test's validity and reliability.

Yet, despite this variability of results and imprecise mechanics, the dependence upon self-assessment models has experienced no decrease in reliance and use among those individuals and institutions seeking to define and utilize personality assessments in order to direct and influence hiring and placement metrics and to facilitate employee congruence within each particular institution. Indeed, corporations large and small, colleges and governmental entities spend hundreds of thousands of dollars every year testing and evaluating their employees, students, and/or job candidates for their motivations, preferences, interests, and styles of interaction in order to more accurately determine each individual's personality type via self-reporting inventories (i.e. questionnaires). This assessment helps the individual and the entities see where individuals may flourish both professionally and/or personally (or both professionally and personally) which in turn manifests as increased job satisfaction and, correspondingly, increased productivity. These tests include, but are not limited to, the Myers-Briggs Type Indicator® (MBTI®), the 16 Personality Factor (PF) test, the Big-Five Factor Markers personality test, and the Birkman Personality and Career Assessment. These tests are executed through questionnaires that are heavily weighted toward an individual's, self-assessment, self-awareness and self-reporting. These individuals and entities, however, have been obliged to accept results of a test that contains highly subjective reporting which, based on the answers provided, has a potentially large degree of rate of error that may create and cause bias in both the test-taker and the test administrator/evaluator. Manifestly, test takers may be influenced to answer the personality assessment questions in a way that they believe will produce a report that is in favor of the position the test taker aspires to hold or influence the test giver in a way favorable to the test taker.

Moreover, these self-reporting inventories carry with themselves a high degree of dependence and reliance by the test giver (or results recipient) that produces results on a limited acceptable range of personality types (typically 5 to 16) with which to make any number of significant decision in the life and/or work of the individual. Clearly, over-dependence and over-reliance by entities on results with such wide variances and set on such a rigid platform invites simultaneous risks for both overinclusion and under inclusion.

Yet, as genetic linkages to personality become more evident and verifiable, so too are these linkages establishing themselves as a valuable tool to attaining a more thorough assessment of personality that is not only producible but also verifiable and reproducible. Correspondingly, as these discrete genomic areas become identifiable, the knowledge and detection of the origins of singular personality traits will allow each individual to pinpoint potential areas of growth and to modify their actions and interactions accordingly. Clearly, advanced or extreme versions of neuroticism, introvertedness, negative emotionality, emotional instability, disagreeableness, negativism, and not being open to new experiences are places that, if identified, may be enhanced or restrained according to desired outcome. In this manner such personality assessments can be used to access both one's strengths and weaknesses thereby accentuating one's positive traits while deemphasizing and modifying the "negative effects" and negative connotations of identified negative traits. By having a clearer idea of what areas necessitating improvement, individuals, schools, and employers can invest in training and environmental changes that may foster growth in these specific areas thus improving individual well-being, productivity and environmental contentment and overall happiness.

With advances in genetic understanding and genetic testing from merely the observational to the scientifically verifiable, genes and gene expression represent a discrete, identifiable and reproducible means to correlate specific genes with certain personality traits. Expressly, genetics has the ability to not only bridge the gap between these well-established, but subjective, personality tests (and the completely human experience of biasing test answers and results) and an individual's personality traits and type, but also to add in detectable and reproducible results in the field of personality psychology.

It has been estimated that a full 30% to 60% of personality can be accurately predicted from a person's genes, which has the potential to operate to (1) dispel, test and/or bolster the legitimacy of self-reported results as a means of accuracy verification, (2) diagnose inconsistencies between self-reporting and genetic predisposition, (3) lead to stronger question sets, (4) allow for the development of targeted testing questions, and (5) provide for a feedback loop that can guide the effective integration of both forms of testing—all leading to an increased reliability and enhanced reliance upon personality tests and their results. Likewise, the interdependence between self-assessment and targeted genetic predispositions has the potential, through a feedback loop described above, to aid in evaluation, understanding and therapy decisions on a more precise scale and via a more scientifically exacting manner that aids both patient and clinician.

Unambiguously, it has only become possible, with the advancement of the mapping of the entire human genome and the ability to analyze large amounts of data (i.e. meta-data), that scientist have been able to move from inheritance studies (measuring genetic linkage within familial structures) to vastly more informative genome-wide association studies (GWAS) in which human genomes may be compared between any 2 individuals or between and among a group of individuals or groups of groups to determine the existence and rate of variations in an individual's nucleotide sequence (SNPs) as well as larger variations (e.g. insertions, duplications, and deletions) and the phenotypic consequences of those variations. Manifestly, any of the aforementioned genetic variations and/or "mutations" have the potential to change that individual's phenotypic, observable and appreciable personality traits via discrete changes in that individual's genetic make-up. It is this data that has provided the necessary tools to analyze each human genome (and correspondingly a vast number of human genomes) in terms of consistencies and inconsistencies and the ability to extrapolate these large data sets into appreciable determinates of personality traits and ultimately personality itself.

In addition to assessing one's personality, traditionally through self-assessment questionnaires, and the novel genetic analysis proposed thus far, we can also verify (and possibly determine) personality type using cyber footprint meta-data. A cyber footprint includes any activity by an individual recorded by a technological device including but not limited to, mobile device, computer, and wearable technology. The data which a user inputs on social media, records on their Fitbit, or googles on their desktop are all identifiers into who the individual is and what they are like. Contextualized genetics is the merger of biology and cyber-activity which can create a more accurate assessment of an individual from their genotype (nature) and phenotype (nurture). This invention includes the biological assessment of personalities, with or without combining meta-data, from the individual's cyber footprint to have a truly granular, in-depth analysis of who the individual is predisposed to be (based on genotype) versus how that individual actually is and/or how he or she actually portrays themselves to be. This assessment of personality based on cyber footprint data is at a smaller risk of bias than the above-mentioned questionnaires taken by individuals who may have both conscious or unconscious objectives in the way they act and respond. The language one uses in social media status updates, the amazon products purchased, and the Pinterest categories followed are more authentic and reliable representations of who a person is as opposed to who they appear to be.

While strides have been made to overcome the inadequacies of linking personality traits with genetic variations and digital (cyber) activities as defined and described through various assessment and self-assessment corroborative tools, it remains evident that considerable failings remain in the field. It is the goal of the present invention to remedy these shortcomings as to allow for the identification and prediction of certain personality traits based, individually, on genetic determinations, assessments and digital activity but, more so to rely on all three determinative tools, in combination, to better assist in accurate determinations and for the allowance of each individual tool to increase the predictive capacity and sensitivity of each other contributing tool. It is the further comprehension of the delicate operations and functions within and between determination tool and their interdependence and reliance upon the other that will best serve inventor's invention and method of use.

While inventor has set forth the best mode or modes contemplated of carrying out the invention known to inventor such to enable a person skilled in the art to practice the present invention, the preferred embodiments are, however, not intended to be limiting, but, on the contrary, are included in a non-limiting sense apt to alterations and modifications within the scope and spirit of the disclosure and appended claims.

BRIEF SUMMARY

Although advantages of the present invention will become readily apparent to those skilled in the art from the following detailed description, there is described herein certain preferred embodiments of the invention and examples for illustrative purposes. Although the following detailed description contains many specific details for the purposes of illustration, one of ordinary skill in the art will appreciate that many variations and alterations to the following details are within the scope of the invention. Accordingly, the following embodiments of the invention are set forth without any loss of generality to, and without imposing limitations upon, the claimed invention. While embodiments are described in connection with the description herein, there is no intent to limit the scope to the embodiments disclosed herein. On the contrary, the intent is to cover all alternatives, modifications, and equivalents.

There are single nucleotide variants (i.e. single nucleotide polymorphisms or SNPs) in DNA, occurring approximately once in 300 nucleotides, that can act as biological markers that can affect gene function and play a role in (1) predicting an individual's response to exogenous drug compounds, (2) determining an individual's susceptibility to environmental influencers, (3) evaluating an individual's risk of developing certain disorders and diseases, and (4) assessing the genetic basis for a predisposition toward certain personality traits and personality types.

While most SNPs have no effect on health or well-being, others, or groups of others, have proven essential to discovering the genetic basis for exhibiting certain personality types and traits. These SNPs can be categorized and subdivided into personality trait indicators and personality determinates defined, generally, by the Five-Factor Model of personality (a.k.a. The Big Five Personality Traits). It is through these distinct five factors ((0) Openness to Experience (i.e. reflected in intellectual curiosity and creativity), (C) Conscientiousness (depicting structure and discipline), (E) Extraversion (denoting an individual that is outgoing and engaging), (A) Agreeableness (i.e. an individual that is warm, friendly and tactful), and (N) Neuroticism (measured by negative feelings including anxiety, depression, dear and frustration)) where the intersection between genetic makeup and personality may be best viewed. Additionally, the inventors seek to merge this genotyping test of personality SNPs, along with self-reported personality test responses, to more accurately predict self-reported results, corroborate self-reported results, efficiently triangulate multi-nodal results and more fully assess an individual's personality on a wide spectrum of individual and group personalities and personality traits.

In general, GWA studies compare two large groups of individuals where one control group and one experimental group would be genotyped for (1) the majority of known SNPs and (2) specific SNPs that are associated with specific personality traits (i.e. those that are associated with one of the Big Five Personality Traits). For each identified SNP in the experimental group, the allele frequency is determined and compared to that of the control group. The odds ratio is then calculated where the ratio of two odds is determined (the odds of those having the personality trait and the allele and those individuals having the personality trait without the allele). The results ratio would then be verified with a self-assessment tool (i.e. questionnaire) to substantiate the results of the self-assessment tool and to further retrospectively increase the accuracy and identification of the genetic testing. It is this reinforcement "feedback loop" that has the greatest potential for a successfully evolving manner and method of developing a symbiotic relationship between genetic and assessment testing.

Once specific SNPs are identified correlating to degrees of exhibition of certain identifiable personality traits (i.e. Conscientiousness, Extraversion, Neuroticism, Openness, and Agreeableness), the degree to which an individual displays those traits are quantified on a scale as a percentage from 0% to 100%. Simply, once identified and given a numerical value, the percentages can be converted to a vector for each user and then plotted spatially. As provided for below, the traditional personality traits (Conscientiousness, Extraversion, Neuroticism, Openness, and Agreeableness) are additional accompanied by persistence, which For example, individual A exhibiting the following traits:
Conscientiousness: 67%
Extraversion: 50%
Neuroticism: 60%
Openness: 35%
Agreeableness: 17%
Persistence: 0%
and
Individual B exhibiting the following traits:
Individual B is
Conscientiousness: 87%
Extraversion: 23%
Neuroticism: 60%
Openness: 35%
Agreeableness: 17%
Persistence: 0%
Where each is converted, spatially, into vector form for each user where:
A=[0.67, 0.5, 0.6, 0.35, 0.17, 0]
B=[0.87, 0.23, 0.6, 0.35, 0.17, 0]

The distance between individual plots can then be calculated wherein the similarity level S=f (A, B), where S can be scaled to be value between 0 to 100%. In the above instance, 0 percent is the least compatible and on hundred percent is the most compatible.

The method of determination can be calculated by a number of means including, but not limited to, cosine similarity, Euclidean distance, related correlations and other like means. By way of example any two things or data objects, here individuals, may be defined and compared based on a variety and any number of factors where similarity (and likewise dissimilarity) may be determined through the use of an algorithmically defined similarity metric. Two such examples appear below:

Cosine Similarity

Examples of determinations of similarity may be derived through Cosine Similarity where coordinates may be plotted as a vector and the similarity between the two is expressed as the angle between two vectors (which can be extrapolated to a plurality of data objects/individuals). A perfect correlation will have a score of 1 (or an angle of 0) and no correlation will have a score of 0 (or an angle of 90 degrees). Depicted mathematically:

$$similarity(A, B) = \frac{A \cdot B}{\|A\| \times \|B\|} = \frac{\sum_{j=1}^{n} A_i \times B_i}{\sqrt{\sum_{j=1}^{n} A_i^2} \times \sqrt{\sum_{j=1}^{n} B_i^2}}$$

Euclidean Distance

Converting to numerical values, the distance between 2 data objects may be determined where attributes (i.e. personality traits) of each data objects are known, and each is capable of normalization (where each is measured as per the same criteria). The Euclidian Distance is then determinable via the following equation:

$$d(p, q) = \sqrt{(p_1 - q_1)^2 + (p_2 - q_2)^2 + \ldots + (p_n - q_n)^2} = \sqrt{\sum_{i=1}^{n}(p_i - q_i)^2}.$$

Subtracting each attribute in individual A from the same attribute in individual B, they are then entered into the above quadrature wherein the shorter the distance the more similar the individuals are.

And while different methods of determining similarity (i.e. compatibility) exist (e.g. Pearson Coefficient, Jaccard Coefficient, Tanimoto Coefficient etc.), the spatial relation is nonetheless derivable through mathematical computation resulting in ascertainment of proximity (closeness or distance) of two individuals. It is within the contemplation of the inventors, though, that multiple means of calculation and computation are available to enable the discernment of individual affinity and compatibility through comparison of genetically identifiable and quantifiable traits.

And while it has come to be accepted that the heritability of personality is polygenic in nature and that genetic variants on multiple sites are thought to be additive and cumulative versus a single SNP being responsible for one identifiable trait, it remains the goal of the inventors to identify the several areas upon the human genome that are the loci of one to a number of candidate genes that hold promise as an indicator of phenotypic personality traits. Among the strongest associations to each personality are as follows:

Openness to Experience/Novelty Seeking

Kim et al.[1] studied 1089 Korean woman aged 18-40 and found the following strongest areas for association to openness: SNP rs2146180 on Chromosome (CHR) 9 at Base Pair (BP) 8035606, SNP rs1879637 on CHR 2 at BP 212576869, SNP rs1561176 on CHR 7 at BP 154639646. While SNP rs4990638 has equally received attention in the area of openness to experience.

Terracciano et al.[2] studied 3972 participants, 2250 women and 1722 men, from Lanusei Valley on the island of Sardinia, Italy and found a close association between SNP rs644148 found on gene ZNF180 on chromosome (CHR) 19 at BP 49662775, SNP rs6610953 on gene FUNDC1 at BP 44156440, SNP rs17819128 on gene CREBL2 at BP 12652926, SNP rs9291420 on gene MIST at BP 10169156, SNP rs1037791 on gene TSPAN13 at BP 16597902 and SNP rs586281 on CHR 1 at BP 182931141. Other SNPs with a likely biological relevance include rs10251794, rs9342730, and rs16895223.

De Moor et al.[3] conducted a meta-analysis of genome wide association data of some 20,669 individuals of European ancestry where SNPs rs1477268 and rs2032794 near the RASA 1 gene on CHR 5 point to areas with a scientifically significant probability related to openness to experience.

Verwij et al.[4] examined the genotypic information from 5117 participants (1727 males and 3390 females) to study Cloniger's temperament scale in order to identify genetic variants underlying personality traits. The investigators found 7 SNPs (within the top 50 SNPs) that were strongly associated with Novelty Seeking (which the inventors have equated with Openness of the Big Five Personality Test). Those locations are as follows:

SNP rs4131099 on CHR 16 at BP location 51330531
SNP rs3120665 on CHR 1 at BP location 152316590
SNP rs961831 on CHR 9 at BP location 22362104
SNP rs1533665 on CHR 15 at BP location 78530940
SNP rs10176705 on CHR 2 at BP location 50744774
SNP rs1835856 on CHR 3 at BP location 116491672
SNP rs7588898 on CHR 2 at BP location 68041842

Conscientiousness

As above, Kim et al.[1] considered not only locations for determination of Openness but further discussed various points on the genome for conscientiousness as well. To this point Kim et al. has cited SNP rs4642987 on CHR 10 at BP location 93711005, SNP rs375092 on CHR 7 at BP location 23381148, and SNP 1873386 on CHR 12 at BP location 18899246 as evidencing the highest correlation to a conscientiousness personality trait.

Terracciano et al.[2] lists SNP rs11626232 on gene SMOC1 on CHR 14 and BP location 69557149, SNP rs10953555 on gene LAMB1 on CHR 7 and BP location 107175297, SNP rs17006841 on gene MRPS18C on CHR 4 and BP location 84734382, SNP rs2835731 on gene DYRK1A on CHR 21 and BP location 37718598, SNP rs13070781 on gene EIF4E3 on CHR 3 and BP location 71836676, and SNP rs10945200 on gene COL19A1 on CHR 6 and BP 70948461 at the top of associations identified in their SardiNIA GWA study.

De Moor[3] has as well found statistically significant results confirming an association for conscientiousness in the KATNAL2 gene on SNP rs2576037 on CHR 18 at BP 47059049.

Lo et al.[5] established a well-founded association with SNP rs3814424 and conscientiousness.

Extraversion

Kim et al.[1] found that SNP rs6791874 had the highest-ranked association SNP consistently present but fell below the researchers P-value threshold. SNP rs17635977 and rs4783307 were not shown to be linked to extraversion by Kim, despite previous reports.

Terracciano et al.[2] found several areas of association that carried with them varying degrees of connection with extraversion including: SNP rs904208, SNP rs2813838, SNP rs11030064, SNP rs16831315, SNP rs4562724, SNP rs644148, SNP rs17635977, SNP rs4783307, SNP rs8056579, SNP rs928114, SNP rs17786591 and SNP rs6265.

Lo et al.[5] describes SNP rs57590327, rs2164273, rs6481128, rs1426371, and rs7498702 as those related to those areas found to exhibit variants significantly associated with personality traits most closely associated with extraversion. Lo et al. likewise found significant loci on 12q23.3 on WSCD2 and identifiable regions near PCDH15 (a member of the cadherin superfamily) and in L3MBTL2 (gene associated with schizophrenia).

Agreeableness

Kim et al.[1] described SNP rs4833624, SNP rs12934132, SNP rs9611312, SNP rs2087017, SNP rs16923100, and SNP rs11219218 as showing the strongest association with agreeableness.

Terracciano et al.[2] identified in the SardiNIA GWA analysis SNP rs1380251, SNP rs2540226, SNP rs6832769, SNP rs602041, SNP 9940706, SNP 11223249, SNP rs2861913, SNP rs10118853, SNP rs7637878 and SNP rs1801260 as being more closely related to agreeableness.

Neuroticism

Perhaps the best studied of the five personality traits is neuroticism—in all likelihood due to its close relation to the negative effects of neuroticism and the number of diagnosable psychiatric and emotional disturbances that are linked to this specific personality trait that exist on a continuum between phenotypic and genotypic expressions (taking in consideration environmental factors). In fact, Lo et al.[5], holds neuroticism out as being inversely proportional to the other four personality traits, which are all positively correlated.

Kim et al.[1] designates SNP rs10106540 3 SNPs: rs265981, rs686, and SNP rs4532 and SNP rs12601685 (exhibiting the strongest signal) as having a close association with neuroticism.

Terracciano et al.[2] describes both SNP rs362584 and SNP rs1849710 as having the strongest association with neuroticism. As well, Terracciano has shown associations of neuroticism with SNPs rs6047641, rs1159275, rs7329003, and rs2039528.

Lo et al.[5] detected the strongest association with neuroticism within a sub region of 8p23.1 Further Lo et al.[5] found a variant in L3MBTL2 with genome-wide corroborated significant associations. Specifically, Lo et al.[5] discovered associations with neuroticism with SNPs rs6981523 and rs9611519.

Finally, Okbay et al.[6] identified several SNPs (rs2572431, rs193236081, rs10960103, rs4938021, rs139237746, rs1557341, rs12938775, rs12961969, rs35688236, rs2150462, and rs12903563) as harboring genome-wide significant associations with neuroticism.

DETAILED DESCRIPTION OF THE PREFERRED EMBODIMENTS

A detailed description of the preferred embodiments of the invention are disclosed and described below. Yet, each and every possible embodiment, within the limits of the specification, are not disclosed as various permutations are postulated to be in the purview and contemplation of those having skill in the art. It is therefore possible for those having skill in the art to practice the disclosed invention while observing that certain concepts and conceptualizations are relative and capable of being interpreted in one of a number of ways that nonetheless accomplishes the identification and remuneration of one or more of the infirmities as outlined and discussed above in the field of personality traits.

Equally, it should be observed that the present invention can be understood, in terms of function, from the accompanying disclosure taken in context with the claims. And whereas the present invention and method of use are capable of several different embodiments, which can be arranged and rearranged into several configurations, which allows for mixing and matching of features and components, each may exhibit accompanying interchangeable functionalities, which may be employed, without departing from the scope and spirit of the present application as disclosed and described.

It is a goal of inventors to provide a genetic basis of personality determination based on four criteria (1) determination of a correlation between identified genetic SNPs and personality traits, (2) current and ongoing determinations of a correlation between identified genetic SNPs and personality traits, (3) newly discovered determinations of a correlation between yet to be identified genetic SNPs and personality traits and (4) a combination of all determinations, both previously defined and yet to be determined, in an effort to track and specify genetic determination of personality traits.

It is yet another goal of inventors to provide a genetic basis in combination with an assessment or self-assessment tool in order to determine the validity of genetic variation in personality determination and to quantify and qualify the genetic variation responsible for the present and absence of certain traits and the frequency and degree to which these traits occur. As well, assessment and self-assessment tools may be used as a means to determine the validity and reliability of genetic determinations of a genetic basis for personality determination.

It is another goal of inventors to combine genetic datasets with large digital datasets such as social media metadata (e.g. cyber footprints of individuals) to more fully un-bias the questionnaire results for personality and personality traits to arrive at a more comprehensive determination of personality types, subtypes and the varied nuances that accompany all of the complexities of human beings' personalities and personality traits. This merger of genetics, cyber footprint and questionnaire is a novel contextualized genetics testing that will more accurately describe and predict an individual's personality.

It is yet another goal of inventors to provide ever strengthening, more precise and consistently reproducible results for directly observable, self-reported and genetically derived data analysis, together, as a communal amalgam that is directed toward an ever improving and enlightened model of genetics-based personality understanding.

It is another goal of inventors to utilize (O) Openness to Experience, (C) Conscientiousness, (E) Extraversion, (A) Agreeableness and (N) Neuroticism as a basis and starting point to better understand these broad categories and their derivation form genetic variations and mutations.

It is another goal of inventors to use cyber foot printing and assessment and self-assessment, in combination with genetic determinants, where cyber foot printing is used to better understand both assessment and self-assessment and genetically based personality determinations, assessments and self-assessments are utilized to gain a better comprehension of cyber foot printing and genetically-based personality determination and genetically-based personality determinations are used to validate and verify assessment, self-assessment and cyber foot printing.

It is still another goal of inventors to delineate and define potential compatibility between and among individuals, individuals and groups and groups and groups through the utilization of contextualized genetics as described above.

These particular embodiments disclosed are merely illustrative, which may be apparent to those having skill in the art that they may be modified in diverse but equivalent manners. It is therefore contemplated that these particular embodiments may be altered and modified and that all such alterations are considered within the scope and spirit of the present application. And while these illustrations are of a limited number set, it is clear that the invention itself is mutable to any number of arrangements, configurations and modifications without departing from the invention's spirit thereof.

REFERENCES

1. Han-Na Kim, Seung-Ju Roh, Yeon Ah Sung, et al. Genome-wide association study of the five-factor model of personality in young Korean women. *Journal of Human Genetics* (2013) 58, 667-674; doi:10.1038/jhg.2013.75; published online 1 Aug. 2013.
2. A. Terracciano, S. Sanna, M. Uda, et al. Genome-wide association scan for five major dimensions of personality. *Molecular Psychiatry* (2010) 15, 647-656; doi:10.1038/mp.2008.113; published online 28 Oct. 2008.
3. Marleen H. M. de Moor, Paul T. Costa, Antonio Terracciano. et al. Meta-analysis of genome-wide association studies for personality. *Molecular Psychiatry* (2012) 17, 337-349; doi:10.1038/mp.2010.128; published online 21 Dec. 2010.
4. Verweij K J, Zietsch B P, Medland S E et al. A genome-wide association study of Cloninger's temperament scales: implications for the evolutionary genetics of personality. Biological Psychology. 2010 October; 85(2): 306-17. doi: 10.1016/j.biopsycho.2010.07.018. Epub 2010 Aug. 4.
5. Min-Tzu Lo, David A. Hinds, Joyce Y. Tung et al. Genome-wide analyses for personality traits identify six genomic loci and show correlations with psychiatric disorders. Nature Genetics. 2017 January; 49(1): 152-156. Published online 2016 Dec. 5. doi: 10.1038/ng.3736
6. Aysu Okbay, Bart M L Baselmans, Jan-Emmanuel De Neve, et al. Genetic variants associated with subjective well-being, depressive symptoms, and neuroticism identified through genome-wide analyses. Nat. Genet. 48, 624-633 (2016); published online 18 Apr. 2016; corrected after print 27 Jun. 2016; corrected after print 29 Aug. 2016

We claim:

1. A method of confirming or identifying personality traits, based on specific loci, number and identifiable variations within an individual's nucleotide sequence in the form of SNPs and comparing those individual SNPs with other individual SNPs or groups of SNPs comprising the steps of:
   collecting a DNA sample from an individual, groups or groups of groups;
   genotyping, sequencing and analyzing said sample or samples for isolation and sequencing of specific SNPs identified as having a correlation, positive or negative, to the expression of a degree of a set of 5 personality traits: Conscientiousness, Extraversion, Neuroticism, Openness, and Agreeableness;
   genotyping, sequencing and analyzing said sample or samples for isolation and sequencing of SNPs, generally, which may have a correlative indication, positive or negative, to the expression of a degree of a set of 5 personality traits: Conscientiousness, Extraversion, Neuroticism, Openness, and Agreeableness;
accessing the SNP profile of a data set of individuals, groups or groups of groups via an open-source genome database;
collecting and downloading the nucleotide sequence of the SNP profile of said data set of individuals, groups or groups of groups and said individual;
expressing said personality traits as a percentage from 0% to 100%;
converting each percentage into a numerical value;
combining numerical values into a numerical value score;
plotting numerical value score into vector form;
comparing each said collected individual SNP plotted profile to every other SNP plotted profile collected, downloaded and plotted spatially;
determining the degree of similarity and dissimilarity of personality traits, via spatial distance, of all collected, download and plotted SNP profiles as evidenced as a score;
comparing said individual SNP profile score to every other SNP profile score from a predetermined matrix of scores; and
equating personality trait similarity and dissimilarity to proximity and spatial distance of each SNP plotted profile.

2. The method of claim 1 wherein said individual SNP profiles are compared to other individual's, group's or database's SNP profiles in order to identify a correlation between a set of identified SNPs to personality traits, determine a correlation between unidentified SNPs to personality traits, or a combination thereof, to establish a range of congruence between SNPs and personality traits defining similarity and dissimilarity of personality traits between and among individuals, groups and groups of groups.

3. The method of claim 2 wherein the individual profile score and every other SNP profile score is combined with observational or self-assessment reporting to generate an overall personality trait similarity score and spectrum of least to greatest degree of similarity.

4. The method of claim 3 wherein genotyping, sequencing and analyzing of SNPs is achieved by reducing an individual's SNPs down to the genetic sequence, aligning said genomic sequences against one another and finding the ratio of congruence and difference between SNPs between two individuals.

5. The method of claim 4 wherein direct assessment and/or observational assessment is combined with and individual's SNP profile score to affirm, corroborate or adjust an individuals' personality profile through assigning weight of said direct or observational assessment and SNP profile score.

6. The method of claim 5 wherein sequencing of specific SNPs identified as having a correlation to certain personality traits, both positively and negatively, are used to affirm, corroborate, or adjust direct observation and/or self-assessment tools.

7. The method of claim 6 wherein direct observation or self-assessment tools are used to affirm, corroborate, or adjust determinations and correlations of certain personality traits with certain SNPs.

8. The method of claim 7 wherein cyber foot-printing is used to affirm corroborate or adjust determinations and correlations of certain personality traits with certain SNPs and direct observation tools and self-assessments.

9. The method of claim 8 wherein identified and unidentified SNPs correlating with certain personality traits are used to affirm, corroborate, or adjust determinations and correlations of certain personality traits with certain cyber footprints, self-assessments and direct observation tools.

10. The method of claim 1 wherein direct observation and self-assessments are used to affirm corroborate or adjust determinations and correlations of certain personality traits with certain cyber footprints and identified and unidentified SNPs.

11. The method of claim 1 wherein the distance between individual plots is calculated wherein the similarity level $S=f(A, B)$, where S can be scaled to be value between 0 to 100% where 0 percent is the least similar and one hundred percent is the most similar.

12. The method of claim 1 wherein spatial relation between plot points equates to affinity and compatibility between individuals.

13. A method of determining personality trait similarity between individuals through contextualized genetics wherein personality traits and degrees of similarity and dissimilarity between and among personality traits are determinable and determined between and among individuals, individuals, groups and groups and groups comprising the steps of:
collecting a DNA sample from an individual, plurality of individuals and/or groups;
genotyping, sequencing and analyzing said samples for isolation and sequencing specific SNPs identified as having a correlation, positive or negative, to the expression of a degree of a set of 5 personality traits: Conscientiousness, Extraversion, Neuroticism, Openness, and Agreeableness;
genotyping, sequencing and analyzing said samples for isolation and sequencing SNPs not identified as having a correlation, positive or negative, to the expression of a degree of a set of 5 personality traits: Conscientiousness, Extraversion, Neuroticism, Openness, and Agreeableness
accessing the SNP profile of a data set of individuals and groups via an open-source genome database;
collecting and downloading the nucleotide sequence of the SNP profile of said data set of individuals and groups;
expressing said personality traits of individuals and groups as a percentage from 0% to 100%;
converting each percentage into a numerical value;
combining numerical values into a numerical value score;
plotting numerical value score into vector form;
comparing each collected SNP plotted profile to every other possible SNP plotted profile collected, downloaded and plotted spatially;
determining the degree of similarity, via spatial distance, between the said collected, download and plotted SNP profiles as evidenced as a score; and
comparing said individual SNP profile score or group SNP profile score to every other individual SNP profile or group SNP profile score from a predetermined matrix of scores to determine presence or absence of SNPs correlated with personality traits, SNPs not correlated with personality traits, or a combination thereof.

14. The method of claim 13 wherein collected SNP profiles are derived via individual, large data sets and genome-wide association studies (GWAS) information.

15. The method of claim 14 wherein consistencies and inconsistencies in self-reporting and direct observations, and the ability to extrapolate information from individuals, large data sets and genome-wide association studies (GWAS) into appreciable determinates of personality traits, are based on collected SNP profiles.

16. The method of claim 13 wherein SNPs, correlated and uncorrelated to personality traits, may be collected and analyzed to determine undefined degrees of correlation between known and unknown SNPs and personality traits.

17. The method of claim 13 wherein determinations of personality traits through collected SNP profiles can be corroborated, analyzed and modified through the collection of cyber foot printing data, direct observation and self-assessment tools.

18. The method of claim 13 wherein the distance between individual plots is calculated wherein the similarity level S=f (A, B), where S can be scaled to be value between 0 to 100% where 0 percent is the least similar and on hundred percent is the most similar.

19. The method of claim 13 wherein spatial relation and distance equates to affinity and compatibility between individuals to individuals, individuals to groups or groups to groups.

* * * * *